(12) United States Patent
Crockford et al.

(10) Patent No.: US 8,820,316 B2
(45) Date of Patent: *Sep. 2, 2014

(54) DRUG DELIVERY APPARATUS

(75) Inventors: David Roe Crockford, Newburyport, MA (US); John Stanley Harold Denyer, West Broyle Chichester (GB)

(73) Assignee: Respironics Respiratory Drug Delivery (UK) Ltd, Chichester (GB)

( * ) Notice: Subject to any disclaimer, the term of this patent is extended or adjusted under 35 U.S.C. 154(b) by 1498 days.

This patent is subject to a terminal disclaimer.

(21) Appl. No.: 10/992,920

(22) Filed: Nov. 19, 2004

(65) Prior Publication Data

US 2005/0087189 A1    Apr. 28, 2005

Related U.S. Application Data

(62) Division of application No. 10/203,337, filed as application No. PCT/US01/04532 on Feb. 12, 2001, now Pat. No. 8,464,706.

(60) Provisional application No. 60/181,852, filed on Feb. 11, 2000.

(51) Int. Cl.
| | | |
|---|---|---|
| *A61M 11/00* | (2006.01) | |
| *A61M 15/00* | (2006.01) | |
| *A61M 11/06* | (2006.01) | |
| *A61M 16/00* | (2006.01) | |

(52) U.S. Cl.
CPC ............ *A61M 11/06* (2013.01); *A61M 15/0088* (2013.01); *A61M 15/0086* (2013.01); *A61M 15/0018* (2013.01); *A61M 11/002* (2013.01); *A61M 2016/0024* (2013.01); *A61M 15/009* (2013.01); *A61M 2016/0036* (2013.01); *A61M 15/008* (2013.01); *A61M 2206/14* (2013.01); *A61M 2205/43* (2013.01); *A61M 2016/0021* (2013.01)
USPC .................................................. 128/200.14

(58) Field of Classification Search
USPC ............ 128/200.14, 200.21, 200.23, 204.24, 128/203.12, 203.13, 203.14, 203.15, 128/203.24, 203.25
See application file for complete search history.

(56) References Cited

U.S. PATENT DOCUMENTS

| | | | |
|---|---|---|---|
| 4,533,082 A | 8/1985 | Maehara et al. | |
| 4,781,871 A * | 11/1988 | West et al. ..................... | 264/4.3 |

(Continued)

FOREIGN PATENT DOCUMENTS

| | | |
|---|---|---|
| EP | 0627266 B1 | 8/1999 |
| GB | 2294402 A | 5/1996 |

(Continued)

OTHER PUBLICATIONS

Simmons et al, "Trends in Compliance with Bronchodilator Inhaler Use Between Follow-up Visits in a Clinical Trial", Chest, Apr. 1996, pp. 963-968.

(Continued)

*Primary Examiner* — Steven Douglas

(57) ABSTRACT

A drug delivery apparatus comprising: a drug delivery device for selectively delivering drug-laden air or air not laden with the drug; a sensor for monitoring the breathing pattern of a patient; a controller arranged to control the drug delivery device to deliver drug-laden air in pulses which begin when the patient is monitored by the sensor to begin inhalation, the pulses having a duration which is adjusted by the controller on the basis of the monitored breathing pattern of the patient; a feedback indicator which indicates to a patient whether the monitored breathing pattern is effective for inhaling drug-laden air or not a dose calculator which calculates the dose delivered to the patient; and an indicator which indicates to the patient when a desired dose has been delivered, whereby the apparatus is configured to deliver the full amount of the desired dose in at least 80% of treatments.

14 Claims, 7 Drawing Sheets

(56) References Cited

U.S. PATENT DOCUMENTS

| | | | |
|---|---|---|---|
| 4,819,629 A * | 4/1989 | Jonson | 128/203.22 |
| 5,093,316 A * | 3/1992 | Lezdey et al. | 514/8 |
| 5,261,601 A | 11/1993 | Ross et al. | |
| 5,301,664 A * | 4/1994 | Sievers et al. | 128/200.23 |
| 5,363,842 A | 11/1994 | Mishelevich | |
| 5,392,768 A * | 2/1995 | Johansson et al. | 128/200.14 |
| 5,508,269 A * | 4/1996 | Smith et al. | 514/38 |
| 5,522,380 A | 6/1996 | Dwork | |
| 5,687,912 A | 11/1997 | Denyer | |
| 5,767,068 A * | 6/1998 | VanDevanter et al. | 514/9 |
| 5,783,433 A * | 7/1998 | Frenz et al. | 435/199 |
| 5,813,397 A | 9/1998 | Goodman et al. | |
| 5,842,468 A | 12/1998 | Denyer et al. | |
| 5,906,202 A * | 5/1999 | Schuster et al. | 128/203.23 |
| 5,935,941 A * | 8/1999 | Pitha | 514/58 |
| 5,993,781 A * | 11/1999 | Snell et al. | 424/45 |
| 6,158,431 A | 12/2000 | Poole | |
| 6,192,876 B1 | 2/2001 | Denyer et al. | |
| 6,237,589 B1 | 5/2001 | Denyer et al. | |
| 6,338,443 B1 | 1/2002 | Piper | |
| 6,367,470 B1 * | 4/2002 | Denyer et al. | 128/200.14 |
| 6,395,300 B1 * | 5/2002 | Straub et al. | 424/489 |
| 6,491,897 B1 * | 12/2002 | Freund et al. | 424/45 |
| 6,518,239 B1 * | 2/2003 | Kuo et al. | 514/2 |
| 6,584,971 B1 | 7/2003 | Denyer et al. | |

FOREIGN PATENT DOCUMENTS

| | | |
|---|---|---|
| GB | 2306891 A | 5/1997 |
| GB | 2316323 | 2/1998 |
| WO | WO-94/071370 | 8/1994 |
| WO | WO-96/00595 A1 | 1/1996 |
| WO | WO-96/07607 A1 | 3/1996 |
| WO | WO-96/09085 A1 | 3/1996 |
| WO | WO-96/12471 A1 | 5/1996 |
| WO | WO-96/13292 A | 5/1996 |
| WO | WO-97/29851 A1 | 8/1997 |
| WO | 9820836 | 5/1998 |

OTHER PUBLICATIONS

Ivanovich et al., "Evaluation of an Auditory Feedback Equipped Metered Dose Inhaler", American Journal of Therapeutics 3, 1996, pp. 818-820.

Kelling et al., "Physician Knowledge in the Use of Canister Nebulizers", Chest, Apr. 1983, pp. 612-614.

Nides et al., "Improving Inhaler Adherence in a Clinical Trial Through the Use of the Nubulizer Chronolog", Chest, Aug. 1993, pp. 501-507.

Bauldoff G. S. et al; "Use of Aerosolized Colistin Sodium in Cystic Fibrosis Patients Awaiting Lung Transplantation", Transplantation, Sep. 15, 1997, vol. 64, Issue 5, pp. 748-752, Clinical Transplantation, XP002505138.

Jensen et al; "Colistin Inhalation Therapy in Cystic Fibrosis Patients With Chronic Pseudomonas Aeruginosa Lung Infection", Journal of Antimicrobial Chemotherapy, 1987, vol. 18, pp. 831-838.

Roberts et al; "Cyistic Fibrosis Inhalation Therapy: Stability of a Combined Salbutamol/Colistin Solution", Autralian Journal of Hospital Pharmacy, vol. 22, No. 5, 1992, pp. 378-380.

* cited by examiner

DRUG DELIVERY APPARATUS

CROSS-REFERENCE TO RELATED APPLICATIONS

This application claims priority under 35 U.SC. §120 as a Divisional of U.S. patent application Ser. No. 10/203,337, filed Nov. 14, 2002, which is the National Stage of International Application No. PCT/US01/04532, filed Feb. 12, 2001, which claims the priority under 35 U.S.C. §119(e) from U.S. Provisional Appl. No. 60/181,852 filed Feb. 11, 2000, all of which are incorporated herein in whole by reference.

BACKGROUND OF THE INVENTION

1. Field of the Invention

The present invention relates to improved drug delivery apparatus, and to the use of improved drug formulations for delivery by the apparatus.

2. Description of the Related Art

A number of drugs have been used for the treatment of patients with respiratory disorders. Antiproteinase inhibitors, such as Prolastin®, are being studied and used in the treatment of inflammatory lung disease and approved for use in congenital emphysema. Prostacylins/prostacylin analogs, such as Iloprost, are used in the treatment of pulmonary hypertension. Mucoactive drugs, such as Pulmozyme® (recombinant, human DNase) and SuperVent®™ are used and studied in the treatment of patients with cystic fibrosis lung disease. Gamma interferon is being studied for use in the treatment of pulmonary fibrosis and tuberculosis. Immunosuppressants, such as cylosporine, are being studied for the prevention of lung organ rejection. The Interferons, specific monoclonal antibodies, directed against tumor-associated antigens, receptors or oncogene proteins, and adenovirus-directed gene therapeutics, are used and studied as a treatment for various lung cancers.

Beta$_2$ adrenergic bronchodilators, such as Ventolin®, Albuterol® and Salbutamol®, are indicated for the prevention and relief of bronchospasm. Corticosteroids, such as Budesonide®, are used in the treatment of inflammatory lung and reactive airways disease such as asthma. Surfactants, such as Exosurf®, Survanta® and Surfaxin™, are used to treat infant respiratory distress syndrome and are being studied as therapies in certain lung inflammatory diseases, such as chronic bronchitis and cystic fibrosis. Anti-infective agents [e.g., antibacterial (e.g., tobramycin); antifungal (e.g., AmBiosome®); and antiviral (e.g., Synagis™, Virazole®, the Interferons and vaccines)] are used to control pulmonary infections, particularly in subjects who are at risk, such as children, the elderly and the immunocompromised and in patients suffering for example with cystic fibrosis lung disease. These latter patients are prone to acute and chronic endobronchial infections, typically caused by the gram-negative bacterium, *Pseudomonas aeruginosa*. *Pseudomonas* infections are treated with the antimicrobial polypeptide, Colistin and the aminoglycoside antibiotic, Tobramycin.

WO 96/12471 discloses the use of an aminoglycoside formulation (Tobramycin) for aerosolisation. The formulation comprises from about 200 mg to about 400 of aminoglycoside dissolved in about 5 ml of solution containing about 0.225% of sodium chloride. The formulation has a pH of between about 5.5 to 6.5 and is administered by aerosolisation. This formulation suppresses and inhibits at least 95% of susceptible bacteria in the endobronchial space of a patient suffering from the endobronchial infection.

Various drug delivery apparatus are suitable for delivering such drugs in atomised form. For example, a jet-type nebuliser is disclosed in WO 96/12471 as being suitable for aerosolisation of the aminoglycoside solution. This nebulises the formulation into an aerosol having a particle size predominantly in the range of 1 to 5 μm. A limited number of nebulisers are suitable for nebulising this formulation. Also, formulations of this kind have quite a large volume, and must be delivered over more than one breath.

The suitable jet-type nebuliser is shown in FIG. 3 of WO 96/12471, and consists of a case, a mouthpiece, a nebuliser cup covered with a cap, a venturi chamber, an air supply tube and a baffle. The liquid formulation is placed in the nebuliser cup, and an air supply tube is connected to it. The pressurised air passes from the cup into a jet nebuliser orifice where an aerosol is created by shearing the liquid solution into small threads of liquid that shatter into small particles when they hit the baffle. As a patient inhales through the mouthpiece, air is drawn in through air intake holes in the cap into the venturi chamber where it mixes with the aerosol and is carried to the patient.

All of the nebulisers disclosed are continuously operating nebulisers which generate an aerosol continuously.

In addition, WO 96/12471 mentions a study of the use of nebulisers to determine the pharmacodynamics of aminoglycoside in the sputum of patients which is a measure of the efficacy of the aerosol delivery. Such jet nebulisers were found to be about 10% efficient under clinical conditions, although the amount deposited and absorbed in the lungs is only a fraction of that 10%. Thus, large quantities of the drug must be used if the required dosage of the formulation is to reach the patient. For this reason, the prior art document is directed to a formulation comprising from about 200 mg to about 400 mg of aminoglycoside dissolved in about 5 mls of solution. This is a large mass of drug to be delivered to a patient, and it means that the treatment must be delivered over a number of inhalations lasting maybe several minutes. An example of ten to thirteen minutes to deliver 300 mgs is given. Single inhalation atomisers, as disclosed in WO 96/09085 and WO 96/13292, are limited to a maximum drug mass per inhalation of less than 10 mgs. Such atomisers are, therefore, not suitable for delivering antibiotics.

Other suitable nebulisers are mesh type nebulisers.

Some drugs, including antibiotics, give no direct feedback to the patient on their effectiveness at the time of inhalation, unlike a bronchodilator for asthmatics which has an immediate effect in easing the patient's symptoms. Further, the inhalation of aerosols, even when appropriately formulated for pH and tonicity may still cause bronchial constriction and coughing in patients. As a result, the patient has no real idea of how much of the drug has been delivered. He or she merely continues to inhale the atomised substance until there is none left.

In a recent study, the connection between the duty cycle in vitro and the inhaled dose during domiciliary nebuliser use has been investigated. The effectiveness of domiciliary nebuliser therapy is determined by the adherence to a prescribed regimen, the deposition of the drug in the appropriate area of the lungs, and the breathing pattern during nebulisation. The breathing pattern of patients was measured in the laboratory, and from those measurements the patient's duty cycle was calculated. The duty cycle is the proportion of the time the patient spends in inspiration and this normally falls in the range of 0.3 to 0.5. If the patient is inhaling aerosol from a nebuliser, then the amount of aerosol that he or she inhales is directly proportional to his duty cycle. This has been confirmed by measurement of the inhaled dose on a filter during testing, and also using lung scintigraphy.

When similar measurements are made during domiciliary nebuliser use, the duty cycle recorded is significantly less than that recorded in the laboratory. This is because the nebuliser output is continuous and patients interrupt their treatment to rest, talk, drink or as a result of disease related symptoms such as coughing. This reduces the amount of drug inspired by the patient. In addition, using the duty cycle to measure dosage does not take account of whether or not the patient has a good inhalation method, nor whether the patient is adherent to that treatment regimen, for example taking the number of treatments prescribed by their doctor. This makes it particularly difficult to assess why a patient does not respond to the treatment, because the doctor does not know whether it is because the patient is not complying with the regimen prescribed, because the patient is not inhaling properly from the delivery system, or because the drug is ineffective. It is quite clear from various studies that a very high proportion of patients are not adherent to their treatment regimen.

Clearly, if the domiciliary duty cycle is much less than the duty cycle measured in a laboratory, the patient is receiving significantly less of the prescribed drug. In addition, a poor inhalation method by the patient and failure to comply with the regimen farther reduce the amount of drug received in the lungs of the patient. The percentage of the predicted dose actually received by the lungs of the patient varies enormously. Typically, less than 10% of the initial volume of drug placed in a nebuliser reaches a patient's lungs in domiciliary use. Thus, it is clear that something of the order of ten times as much of the drug is required to be atomised as actually reaches the patient's lungs.

A number of different types of apparatus for delivering a drug into the lungs of a patient are known. The pneumatic or jet-type nebuliser is particularly effective in supplying an aerosolised drug for inhalation, but other types of nebulisers are available, such as the ultrasonic-type nebuliser in which the drug to be atomised is forced through a mesh by a vibrating piezo-electric crystal whereupon the droplets passing through the mesh are entrained in the air being inhaled by the patient. The mesh gauge determines the size of the droplets which enter the air stream. Alternatively, a dosimetric spacer can be used. When using a spacer, the drug is introduced into the holding chamber of the spacer either in aerosolised form, or by loading the air within the holding chamber with the drug in powdered form. The patient then breathes from the holding chamber, thereby inhaling the drug-laden air. Such spacers are particularly effective when treating children or elderly patients, and for use with certain drugs. The drug is normally delivered over a number of breaths. Of course, the concentration of the drug in each breath decreases over time as a result of dilution caused by ambient air entering the holding chamber to replace air being inhaled by the patient, and as a result of the deposition of the drug within the chamber.

SUMMARY OF THE INVENTION

According to a first aspect of the present invention, a drug delivery apparatus comprises a drug delivery device for selectively delivering drug-laden air or air not laden with the drug; a sensor for monitoring the breathing pattern of a patient, a controller arranged to control the drug delivery device to deliver drug-laden air in pulses which begin when the patient is monitored by the sensor to begin inhalation, the pulses having a duration which is adjusted by the controller on the basis of the monitored breathing pattern of the patient; a feedback indicator which indicates to a patient whether the monitored breathing pattern is effective for inhaling drug-laden air or not a dose calculator which calculates the dose delivered to the patient on a breath-by-breath basis; and an indicator which indicates to the patient when a desired dose has been delivered, whereby the apparatus is configured to deliver the full amount of the desired dose in at least 80% of treatments. As a result of these features of the drug delivery apparatus, the desired dosage is delivered in at least 80% of treatments. This is a result of the combination of a number of factors, including the delivery of drug-laden air only in the part of the inhalation phase which reaches the lungs, and also as a result of the patient receiving an indication as to whether or not he or she is inhaling properly. It is also important to indicate to the patient when the appropriate dose has been delivered. The delivery of the full amount of the dose in at least 90% of treatments, or preferably in at least 90% of treatments is a huge improvement over delivering apparatus which has hereto been used. This improvement offers a number of advantages since almost all of the drug which is delivered is delivered correctly to the correct part of the lungs. This means that considerably less of the drug formulation is required than with existing atomisers. This reduces the cost of the drug, and also shortens the amount of time in which delivery must take place. It may require less than one third of the number of breaths to inhale the correct dose when the apparatus according to the present invention is used over prior art delivery apparatus. In addition, because the apparatus reacts to the patient in order to optimise the length of the pulse in which drug-laden air is delivered, the apparatus is ideal for domiciliary use instead of use merely in hospital. Thus, considerable advantages are received by using the present invention.

It is preferred that the apparatus includes a data log for recordal of information relating to each treatment, including the dose which was delivered. This also adds to the advantages of domiciliary of the apparatus since a doctor can later review the data from the data log to see how well the patient, in fact, complied with the treatments, but in terms of the number of treatments which the patient has taken, and the dose actually received during each of those treatments.

The drug delivery device may be any device which delivers the drug into the lungs of a patient over multiple inhalations. For example, it may be dosimetric spacer including a receptacle defining a holding chamber, a mesh-type atomiser, or a pneumatic-type atomiser.

Other advantageous features are recited in the dependent claims.

The use of such an aerosol delivery system, which only causes atomisation of the drug during inhalation, and adapts to the patient's inhalation pattern significantly reduces the volume of drug required since there is significantly less wastage because no aerosol is generated on exhalation. A particularly surprising effect of the use of such a delivery device is that there is a substantial increase in patients' compliance with the treatment regimen By compliance, it is meant that patients adhere to the prescribed regimen by actually taking prescribed doses at the right time. It is believed that such a delivery system results in more than 90% of treatments being taken correctly until the device signals that the patient has achieved the correct treatment. Unexpectedly high levels of compliance result from this system, so the present invention gives a significant and unexpected advantage compared with other delivery systems. Whereas only about 10% of the volume of drug placed in a conventional nebuliser reaches a patient's lungs, and it is lower in the case of domiciliary use, the present invention means that the amount of drug placed in the nebuliser will fall by approximately 50%. This will lead to significant reductions in drug costs, and will also mean that it will take a much shorter time for the required drug to be administered to a patient.

BRIEF DESCRIPTION OF THE DRAWINGS

Embodiments of the present invention are described below by way of example, and with reference to the drawings in which:

FIG. 10 shows a two-part drug package for supply of the drug.

DETAILED DESCRIPTION OF THE EXEMPLARY EMBODIMENTS

Figure 1:
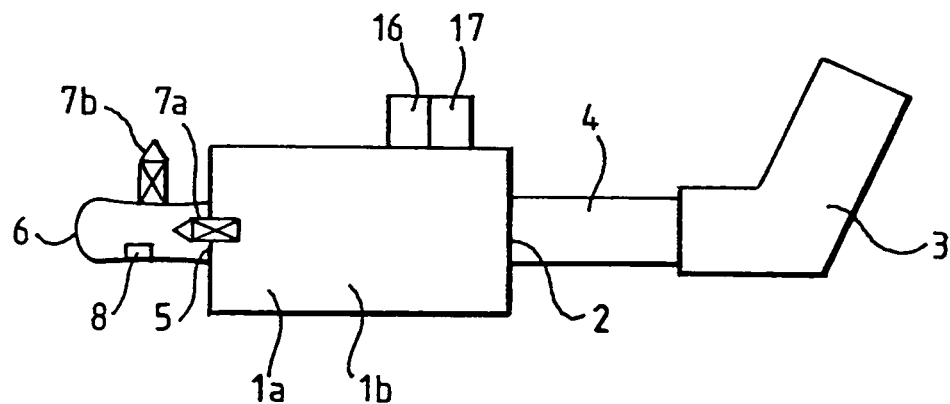
FIG. 1 is a schematic diagram of a dosimetric spacer according to the present invention.

Referring to FIG. 1, a housing 1a defines a holding chamber 1 which includes an inlet 2 through which a liquid or dry powder drug passes into the holding chamber from a source of droplets or particles, for example, a multi-dose inhaler (MDI) 3. The MDI 3 releases the liquid or powder drug in a cloud such that it loads the air with the drug. A sensor 4 is disposed between the MDI 3 and the holding chamber 1 which detects each actuation of the MDI 3. The sensor 4 also detects the rate at which air or other gas enters the holding chamber 1 via the inlet 2.

The holding chamber 1 also includes an outlet 5 to which a mouthpiece 6 is attached. A patient inhales from the mouthpiece 6 drawing air or gas laden with the drug from the holding chamber. This causes ambient air or gas to be drawn into the holding chamber 1 via the inlet 2. The rate of flow of air through the inlet 2 is detected by the sensor 4.

A first valve 7*a* is disposed between the outlet 5 and the mouthpiece 6 through which drug-laden air passes when the patient inhales. A second valve 7*b*, is disposed in the mouthpiece 6 which permits exhaled air to be vented to atmosphere. A controller (described in more detail below in connection with FIG. 4) operates to control both the first and second valves (7*a*, 7*b*). The first valve must be closed during exhalation so that exhaled air does not enter the holding chamber 1. A second sensor 8 is located in the mouthpiece in order to monitor the breathing pattern of the patient. The controller operates the first and second valves 7*a*, 7*b* on the basis of the monitored breathing pattern. When the patient begins to inhale, the second sensor 8 detects this and the controller operates the valves such that the first valve 7*a* is open and the second valve 7*b* is closed in order that the patient inhales drug-laden air from the holding chamber 1. Once the controller decides that no more of the drug-laden air is to be delivered to the patient, or the patient stops inhaling, the first valve 7*a* is closed and the second valve 7*b* is opened such that the patient finishes any remainder of the inhalation with ambient air which enters the mouthpiece via the second valve 7*b*, and exhales through the mouthpiece such that the exhaled air is vented to atmosphere via the second valve 7*b* and does not enter the holding chamber 1. The controller allows inhalation of drug-laden air from the holding chamber 1 in pulses, the duration of which are adjusted according to the monitored breathing pattern of the patient. The controller also analyses the breathing pattern of the patient to ensure that inhalation is suitable for delivering the pulse of drug-laden air. If it is too weak, or too unsteady, the pulse of drug-laden air will not be delivered, or will stop early.

Two indicators 16 and 17 are included in this spacer. The first indicator 16 is a patient feedback indicator which indicates to a patient whether or not suitable inhalation is taking place. In this embodiment, the feedback 16 is a vibrator unit which vibrates gently during inhalation while drug-laden air is delivered. As soon as the first valve 7*a* closes and the second valve 7*b* opens, the feedback indicator 16 will turn off. Also, if the patient does not inhale properly, the feedback indicator 16 will either stop vibrating or will not start vibrating. Thus, a patient will quickly learn how to inhale correctly when using the spacer. The feedback indicator could alternatively be an audible indicator emitting, perhaps, a hum while drug-laden air is being delivered, or a visible indicator such as an LED which lights when drug-laden air is delivered.

The second indicator 17 indicates when the patient has received a full dose of the drug, and when treatment has ended. This could be an audible indicator such as a small speaker emitting a tone, or a visual indicator, such as an LED. Of course, if appropriate, the feedback indicator 16 and the second indicator 17 could be combined into a single indicator, preferably a vibrator or a source of an audible signal.

Once the drug has been released into the holding chamber 1, its concentration decreases, firstly as a result of deposition as the drug settles on the walls and base of the holding chamber due to gravity and electrostatic forces between the housing 1*a* and the drug, and secondly as a result of dilution caused by air entering the holding chamber via inlet 2 to replace drug-laden air inhaled by the patient.

Calculations must be carried out by a dose calculator (not shown) in order to determine the dose of the drug which has actually been delivered to the patient. Details of these calculations are made in our earlier joint patent application published under WO 96/13294, the contents of which are hereby imported into this specification in its entirety. In summary, the dose calculation is carried out on a breath-by-breath basis, the amount of the drug delivered in a breath being added to the amount delivered in each previous breath until the desired dose has been delivered. At that stage, the dose calculator causes the second indicator 17 to indicate that treatment has ended, and the controller no longer allows delivery of the drug-laden air. In addition, the dose calculator includes a formulation input since the spacer can be used for various different drug formulations. The formulation input could be in the form of buttons on the spacer by which the drug formulation being used may be selected. More details of the dose calculator are described in connection with FIG. 4.

A further spacer embodiment is shown in FIG. 2. This spacer is arranged to operate specifically in conjunction with dry powder inhalers (DPI's). DPI's are normally actuated by the patient's inspiratory flow. They are not suitable for patients with a very low inspiratory flow since the DPI is unlikely to be triggered reliably. DPI's release the drug in the form of a fine powder which is inhaled by a patient into his or her lungs. As with conventional MDI's conventional DPI's suffer from the disadvantage that much of a given dose impacts on the back of a patient's throat. Referring to FIGS. 2 and 3, a housing 1*a* defines a holding chamber 1, and includes a first port 9 which is used both to load and empty the holding chamber 1. The spacer also includes a piston 10 movable within the chamber 1. As the piston 10 is drawn back, air or gas is sucked into the holding chamber 1 via the first port 9, and air trapped behind the piston escapes through a second port 11.

Figure 2:
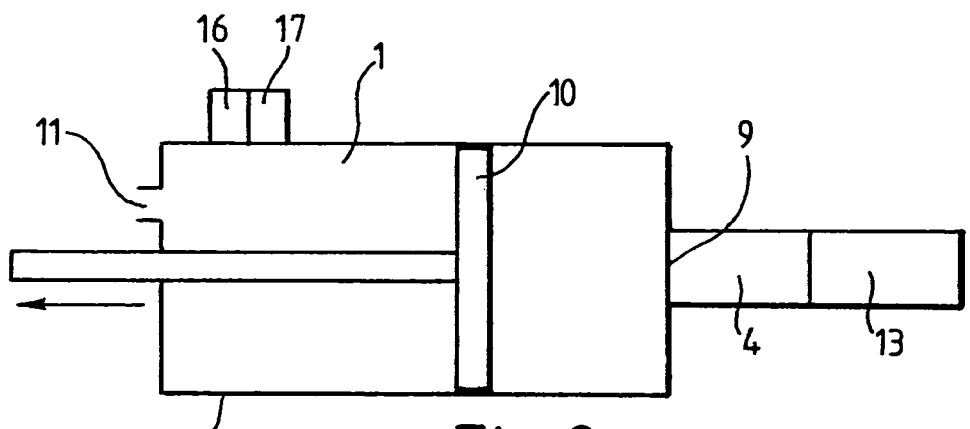
FIGS. 2 and 3 are schematic diagram showing a second form of dosimetric spacer in which a piston is movable through the holding chamber.
Figure 3:
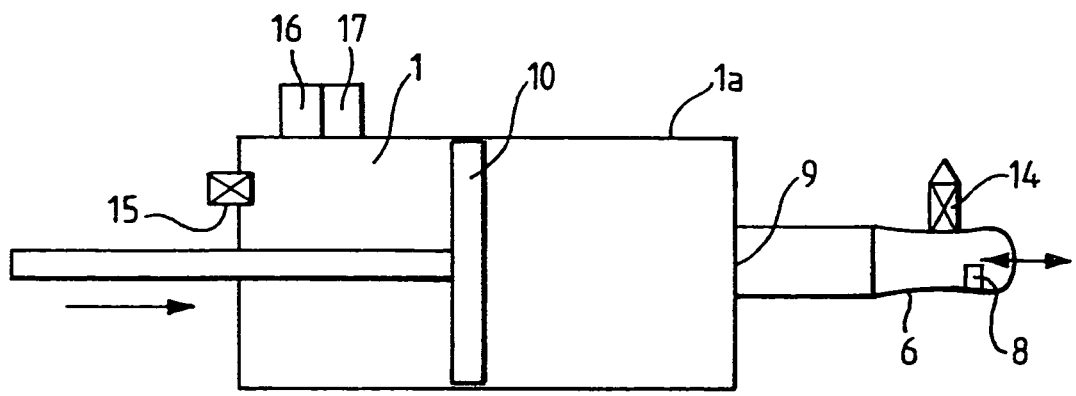

In use, and as shown in FIG. 2, the piston 10 is pulled back drawing air or gas into the holding chamber 1 through the first port 9. Before reaching the first port 9, the air or gas passes through a dry powder inhaler 13 which releases the drug into the air or gas, and over a sensor 4. The piston 10 is fixed in the retracted position. The patient then removes the DPI 13 and replaces it with a mouthpiece 6 as shown in FIG. 3. The patient then inhales via the mouthpiece 6 and the air or gas loaded with the drug is sucked from the holding chamber passing through the port 9, over the sensor 4 and through the mouthpiece 6. The sensor 4 detects this airflow.

The piston 10 returns across the holding chamber 1 as the patient inhales, and is arranged to move only in the direction of emptying the holding chamber 1 to prevent dilution. To permit the patient to exhale, a one-way valve 14 is disposed in the mouthpiece 6. The mouthpiece 6 also includes a second valve 15 which is controlled by a controller (described below) such that when drug-laden air is not delivered during inhalation of the patient, the valve 15 is opened to allow ambient air to enter the mouthpiece before inhalation by the patient. As will be explained below, this allows the drug to be delivered in pulses. Thus, the controller operates the valve 15 on the basis of information received from the sensor 4 which monitors the breathing pattern of the patient. When it detects a patient inhaling correctly, the controller closes valve 15 so that the patient inhales from the holding chamber 1. Once the pulse of drug for that breath has been received, the valve 15 will open again so that ambient air and not drug-laden air is received by the patient. The duration of the pulse is determined by the controller to optimise the delivery of the drug. During exhalation, the exhaled air is exhausted through the one-way valve 14. It will be noted that, since no ambient air enters the holding chamber during inhalation, any reduction in concentration of the drug within the holding chamber is a result of deposition of the drug within the chamber.

As in FIG. 1, two indicators 16 and 17 are present. A patient feedback indicator 16 indicates to a patient whether or not suitable inhalation is taking place, and the second indicator 17 indicates when a patient has received the full dose, and that treatment has ended.

Calculation of the dose given to the patient is now described in connection with the embodiment shown in FIGS. 2 and 3. The patient firstly connects the DPI 13 to the port 9. The piston 10 is pulled back drawing air into the holding chamber 1 via the DPI 13 and the port 9 so that the holding chamber is charged with the drug. The sensor 4, which might be a microphone or a pressure detector, detects this introduction of the drug into the holding chamber 1 and produces a signal. The dose calculator (not shown) receives the signal from the sensor 4 and starts a clock (not shown). The patient then removes the DPI from the port 9 and replaces it with a mouthpiece (FIG. 3). The patient inhales through the mouthpiece, and the air flows past the sensor 4. The dose calculator calculates the amount of the drug delivered to the patient very frequently, typically every one hundredth of a second. The concentration of the drug within the holding chamber 1 is continuously calculated to take account of the deposition of the drug on the walls of the holding chamber 1 over time. A memory contains a data look-up table which gives the concentration of the drug in the chamber 1 at a time after its introduction. The dose of drug inhaled is then calculated by multiplying the volume of air sensed by the sensor 4 by the concentration of the drug at that time. The dose calculated during this one hundredth of a second sample period is then added to the dose calculated in calculations for previous sample periods. The calculation could, alternatively be calculated on a breath-by-breath basis. Once the cumulative total dose reaches a predetermined level, an indication is made to the patient that the full dose has been given via the second indicator 17.

Figure 4:
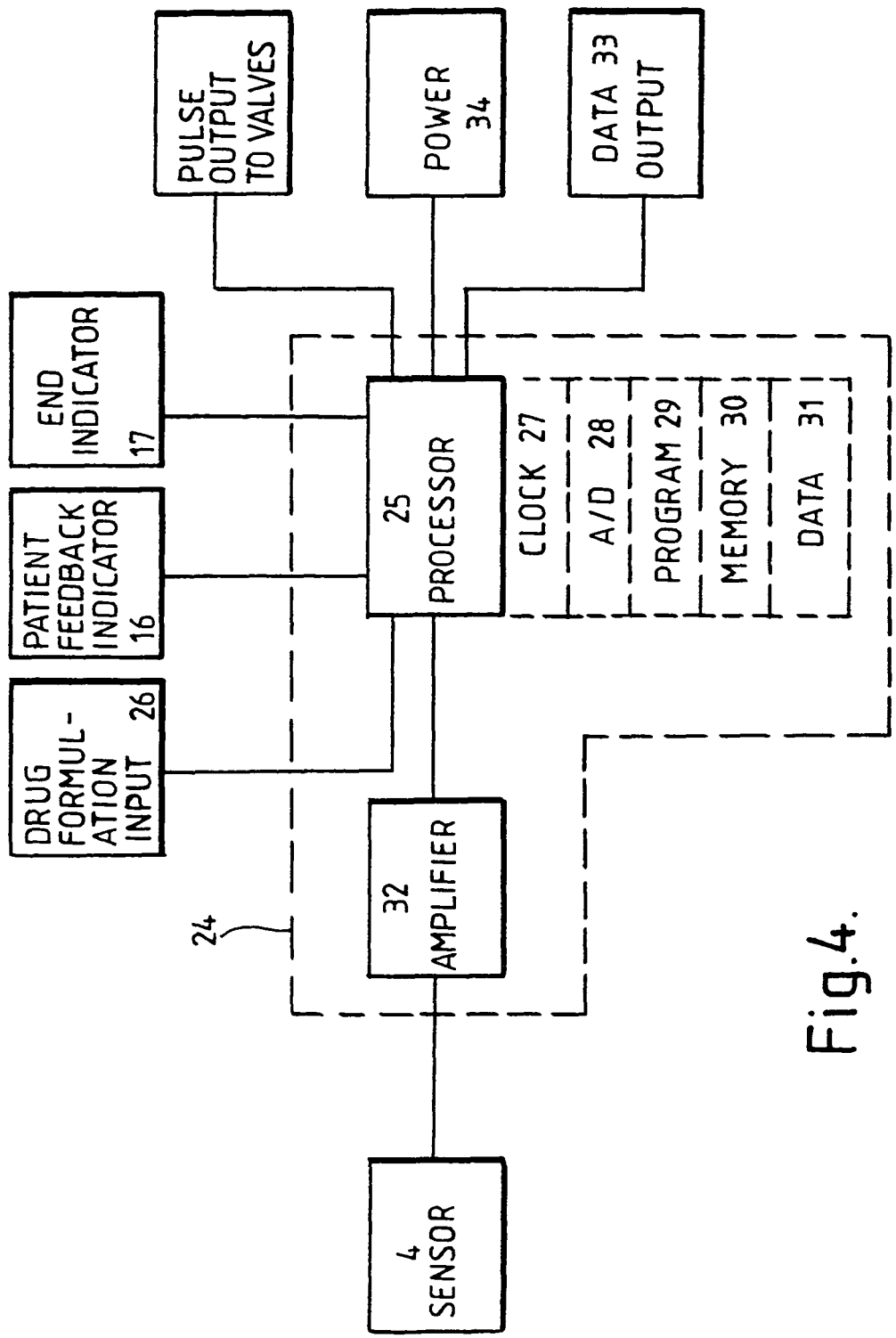
FIG. 4 is a block diagram of a controller for controlling the operation of the second embodiment shown in FIGS. 2 and 3.

FIG. 4, shows a block diagram of the controller 24 for the spacer shown in FIGS. 2 and 3, but which would also be suitable for the spacer shown in FIG. 1. The controller 24 includes a processor 25 powered by a power supply 34. The sensor 4 sends signals to the processor 25 via an amplifier 32 to indicate when the drug is being introduced into the holding chamber 1, and the rate of inhalation of the patient. The processor 25 calculates the dose given to the patient on the basis of a program 29, a memory 30 containing look-up data 31, and a clock 27. Before treatment starts, it is necessary to enter the drug formulation which is being delivered. One way of doing this is for the apparatus to include a drug formulation input 26 which is in the form of buttons on the apparatus. The apparatus may be suitable for delivering any of a number of drugs to a patient and pressing a button allows the processor 25 to take account of whatever formulation is being used. Information regarding drug formulations is stored in the memory 30. The processor 25 will normally calculate the amount of drug delivered to a patient on a breath-by-breath basis, adding the dose detected to have been delivered in one breath to the amount delivered in each preceding breath. This may be done by sampling the air flow on a regular basis during inhalation. Once the processor has calculated that the predetermined dose has been given, a signal is output to the end indicator 35, and treatment is stopped such that the patient can only inhale ambient air through the mouthpiece, and not medication-laden air.

The processor 25 also analyses the breathing pattern such that, if during inhalation, the patient is breathing correctly, the patient feedback indicator 16 is caused to indicate to the patient that correct inhalation is taking place. Correct inhalation might be considered to take place where the inhalation is above a certain strength, or is of suitable stability. In analysing the breathing pattern, the processor 25 also generates a pulse during which drug delivery takes place. The pulse will not take place, or will be terminated early, if the breathing pattern is not considered to be suitable. Thus, the patient feedback indicator 16 can be caused to indicate to the patient only when correct inhalation is taking place during delivery of the drug. If inhalation becomes unsuitable for drug delivery during a pulse, the pulse will be terminated early, and the patient feedback indicator 16 will no longer indicate to the patient that correct inhalation is taking place.

In order to deliver the drug in the most effective manner, the processor 25 analyses each breath, and on the basis of the previous breath or breaths, controls the valves so as to deliver the drug in pulses into only a part of the inhalation phase of the patient. The processor includes a pulse generator (not shown) which generates pulses during which the drug is delivered. The pulse generator controls when each pulse begins and its duration. For example, the pulse of drug delivery may occur in the first 50% of the inhalation phase of a patient. However, the duration of the patient's inhalation phase may vary from treatment to treatment, and even during a single treatment. Thus, the processor 25 must adapt to this change. For example, if the processor is generating pulses of drug delivery which correspond to the first 50% of the inhalation phase, it will need to determine the length of the previous breath or a number of the previous breaths using the clock 27.

On the subsequent breath, the pulse length generator of the processor 25 can generate a pulse as soon as it receives a signal from the sensor 4 that the patient has begun to inhale. The length of the pulse will be 50% of the length of the preceding inhalation phase, or 50% of an average of for example, the preceding three inhalation phases. If the patient fails to inhale correctly, the processor 25 will stop the pulse and indicate to the patient that his or her inhalation is not suitable. The processor 25 controls the valves as described in relation to FIGS. 1 to 3.

Alternatively, the pulse length may be increased to more than 50%, and a description of a further arrangement in which the pulse length is maximised is described in a later embodiment of this invention. Such an arrangement can be applied to the dosimetric spacer.

The memory 30 can also be utilised to record the dose delivered by the apparatus during each treatment. The processor 25 acts as a dose calculator during each treatment to calculate the dose delivered on a breath-by-breath basis. At the end of a treatment, whether as a result of the full dose being delivered, or as a result of the patient stopping treatment prior to a full dose being delivered, the dose actually delivered is recorded in the memory 30 so that at a later date, a doctor or other person can review the dose received by the patient so as to see whether or not that patient was compliant with the treatments. If, for example, the patient has not responded to treatment, it is possible for a doctor to tell whether or not compliance with the regimen has been adhered to, and if so, a different treatment may be prescribed. Thus, the memory 30 also constitutes a data log of treatments. It will normally also record the time when each treatment was administered, and might even include information on the patient breathing pattern if required.

Reference has been made above to look up tables which give data on how concentration of the drug decreases in time, and how concentration of the drug decreases by dilution caused by inhalation of known volumes. The data in the look-up tables must be gathered by experiment. For example, when the data for decrease in concentration of the drug with time is gathered, a known amount of the drug is introduced into the holding chamber, and the air in the holding chamber 1 is then expelled after a time into the filter paper. The expelled drug is then weighed. This experiment is repeated for different time periods to establish the necessary data. The variation of concentration with time profile is likely to be different for different drugs. Therefore the apparatus must have the correct profile programmed in.

Figure 5:
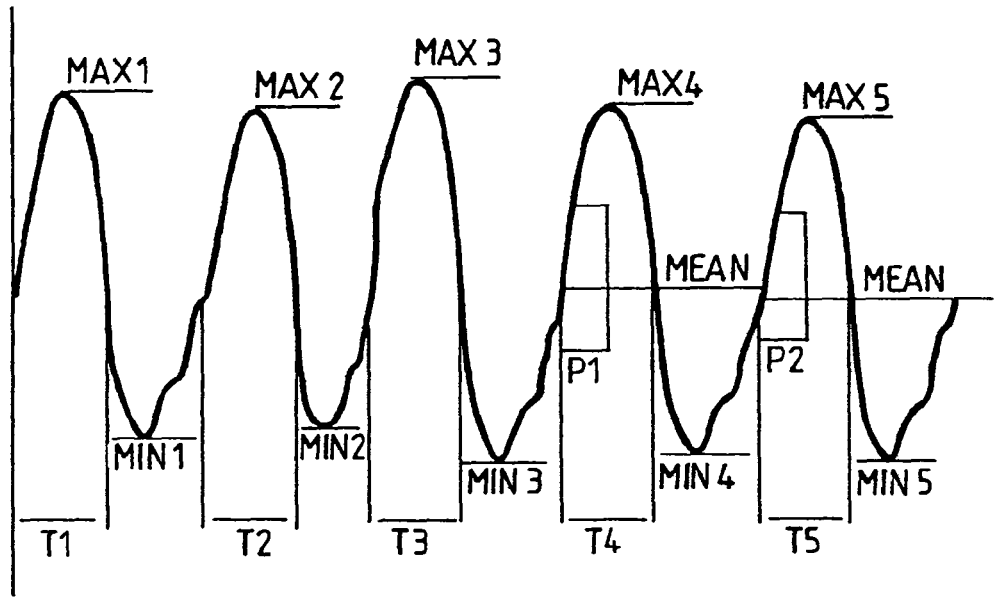
FIG. 5 is a graph showing a breathing pattern of a patient.

A nebuliser according to the present invention will now be described. In order to appreciate the invention, reference is made to FIG. 5 in which the inhalation pattern of a patient is shown over time. It will be appreciated that breathing patterns are not very regular, and that some breaths are deeper than others.

Figure 6:
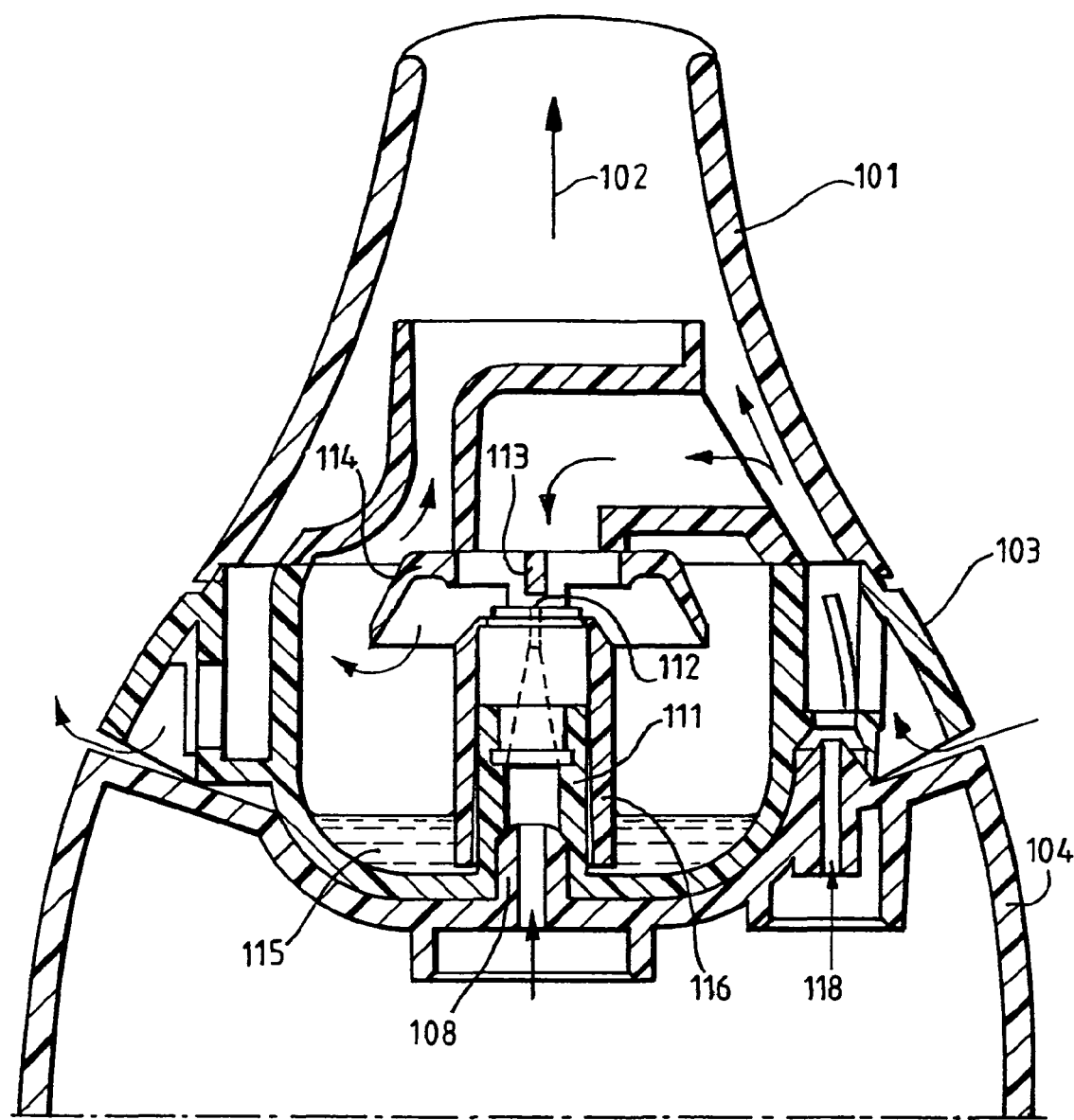
FIGS. 6 and 7 show the upper and lower parts of a nebuliser according to a further embodiment to the present invention.
Figure 7:
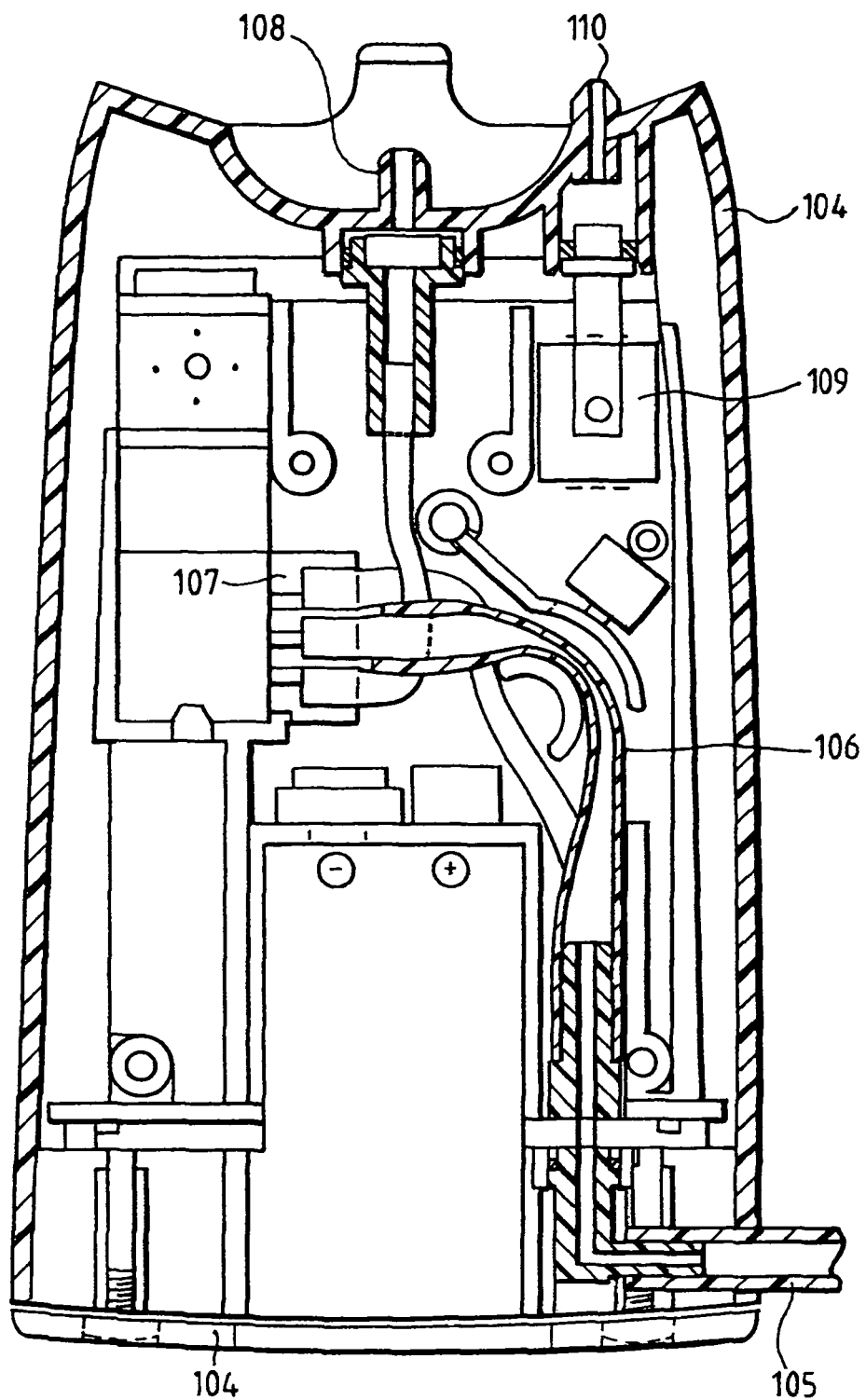

FIGS. 6 and 7 of this application show a nebuliser. Referring to FIG. 6, a mouthpiece 101 is shown through which a patient inhales in the direction of arrow 102. Below the mouthpiece 101 is a removable atomising section 103 which, in turn, rests on a base 104.

The base 104 is shown in more detail in FIG. 7. Referring to FIG. 7, the base 104 includes an inlet 105 through which air is supplied under pressure from a compressor (not shown). The pressurized air is led via a tube 106 to a manifold 107 which controls the flow of pressurized air to an air outlet 108 which directs air into the atomising section 103 shown in FIG. 6. The base 104 also includes a pressure sensor 109 which detects the pressure within the atomising section 103 via a port 110.

Referring again to FIG. 6, air under pressure passes through the air outlet 108 of the base 104 and is conducted through a tubular post 111 to an atomiser nozzle 112 out of which the air issues under pressure. A deflector 113 is located in the path of the pressurised air issuing from the nozzle 112 so that the pressurized air is deflected laterally so as to pass beneath a baffle 114. The passage of the pressurized air across the top of the tubular post 111 causes a drug 115 to be drawn up between the outer surface of the tubular post 111 and the inner surface of a sleeve 116 which surrounds the tubular post 111. The drug 115 is atomised in the stream of air, and carried away in the stream of air below the rim of the baffle 114 and up through the mouthpiece 101 to a patient.

The pressure sensor 109 in the base 104 monitors the breathing pattern of a patient, and on the basis of the breathing pattern, the manifold 107 is controlled to supply pressurized air to the atomising section 103 in pulses only during the first 50% of an inhalation phase so that drug delivery only occurs during that pulse.

This invention applies to atomisers which generate drug delivery pulses. The invention is not, however, limited to the exact atomiser described above, but may be applied to other atomisers. For convenience, the description below of the present invention will refer to components of the device shown in FIGS. 6 and 7, but it can be applied to other atomisers, such as other designs of jet nebulisers, ultrasonic atomisers and pressure mesh atomisers.

Jet nebulisers are of two kinds, these being air-jet nebulisers and liquid jet nebulisers. An example of an air-jet nebuliser, which uses a source of compressed air to nebulise a liquid, is disclosed in EP 0627266 (Medic-Aid Limited), the content of which is incorporated herein in its entirety by reference. An example of a liquid-jet nebuliser, which drives a liquid through one or more nozzle outlets to produce a spray of fine droplets is disclosed in WO 94/07607 (Boehringer Ingelheim International GmbH et al), the content of which is incorporated herein in its entirety by reference.

Ultrasonic nebulisers nebulise a liquid drug using ultrasonic waves usually generated with an oscillating piezo-electric element and take many forms. These include nebulisers 1) where liquid is in direct contact with the piezo-electric element, 2) where there is an amplifying interface, typically an enclosed fluid, between the piezo-electric element and the liquid, and 3) where the piezo-electric element vibrates a mesh from which an aerosol is generated. Examples of ultrasonic nebulisers are disclosed in U.S. Pat. No. 4,533,082 (Maehara et al) and U.S. Pat. No. 5,261,601 (Ross et al), the contents of which are incorporated herein by reference. The nebulisers described in those documents include a housing that has a reservoir which holds a quantity of liquid to be dispensed, which housing has a perforated membrane in contact with the reservoir and an ultrasonic vibrator connected to the housing to vibrate the perforated membrane. Another example of an ultrasonic nebuliser is described in WO 97/29851 (Fluid Propulsion Technologies, Inc), the contents of which are incorporated herein by reference. An example of a pressure mesh nebuliser, which may or may not include a piezo-electric element, is disclosed in WO 96/13292 (Aradigm Corporation), the contents of which are also incorporated herein by reference.

As mentioned above, all of the above types of nebuliser can be used to atomise the drug in pulses. This means that atomisation and drug delivery can be switched on and off. The pulses can be controlled so that atomisation only occurs during a part of the breathing pattern of a patient in which it will be of benefit. With reference to the device shown in FIGS. 6 and 7, the sensor 109 is extremely important in that this measures the breathing pattern of the patient. A controller (not shown) receives the breathing pattern information from the sensor 109 and analyses the breathing pattern of the patient. It will calculate the length of time in which the patient inhales, and on the basis of that information will control the manifold 107 such that atomisation only occurs in a pulse of drug delivery during a part of the inhalation of the patient.

The controller may be of the same form as that disclosed in FIG. 4. In that arrangement, the controller includes a processor 25 which carries out a number of functions, acting as generator of pulses of drug delivery, a dose calculator for calculating the dose delivered on a breath-by-breath basis, and a breathing pattern analyser for analysing the breathing pattern of a patient and, determining whether or not the patient is breathing correctly so that a feedback indicator can be used to indicate to the patient whether or not correct inhalation is taking place. In addition, the processor can take account of different formulations provided that the apparatus includes an input for entering the drug formulation being used. The controller can also log information concerning the treatments, such as the dose delivered, when each treatment was delivered, and information on the breathing pattern of the patient.

For example, a good arrangement is to generate a pulse of drug delivery only in the first 50% of the inhalation of the patient. Since the duration of inhalation of a patient varies between treatments, and also within a single treatment, it is necessary to monitor the duration of inhalation over one or more breaths so that the average duration of inhalation can be calculated in order that the pulse length can be determined for the next breath. Once determined by the controller, as soon as the controller receives an indication from the sensor 109 that inhalation has started, it will generate a pulse of drug delivery equal to half of the average duration of inhalation of the patient. In addition, the inhalation of the patient is analysed to ensure that it is suitable for delivering the drug. If the breath is too weak or is interrupted, or is very uneven in strength, the pulse of drug delivery will not begin, or will be terminated early. To assist the patient in knowing what is a suitable breath and what is not, the nebuliser includes a patient feedback indicator (not shown) which indicates to the patient either that the breath is suitable, or that it is unsuitable. This may be a visual or audible indicator, or even a small vibrator. It is preferred that the nebuliser indicates when a patient is inhaling correctly, and the signal received by the patient could coincide with the pulse of atomisation. In this way, if the inhalation is not suitable, the pulse of atomisation is stopped, and the indication that the patient is inhaling correctly will also be stopped.

An end indicator (not shown) is also included which indicates to the patient when the full dose has been dispensed. To do this, the atomiser also includes a dose calculator which calculates the amount of the drug received by the patient on a breath-by-breath basis. The output of the device will be known through experimentation so that the total length of the pulses can be multiplied by the output rate of the nebuliser to give the total dose received by the patient. Once the dose calculator has determined that the full dose has been delivered, the end indicator indicates to the patient either audibly or visibly that treatment has ended. The controller will not then generate any further pulses for that treatment.

Extending the proportion of the inhalation of the patient in which atomisation takes place above 50% results in the patient receiving their treatment faster since it will take fewer breaths to deliver the required volume of medication. However, to avoid wastage of the medication which is atomised in the end volume of patient's inspiratory volume, the pulse of atomisation must be stopped before the end volume is reached. The end volume is the volume of air inhaled by a patient at the end of the inspiratory volume which remains in the upper airways (the mouth and trachea) and does not enter into the lower parts of the lungs. Any drug which is atomised into the end volume is wasted when the patient exhales, together with any atomised drug left in the nebuliser, since it does not reach the lungs.

The end volume is the volume of the patient's upper airway, and is proportional to the size of the patient. Clearly, the end volume will vary as a percentage of the inspiratory tidal volume since the tidal volume changes significantly depending on the type and extent of the respiratory disease suffered by the patient. The optimum duration of an atomisation pulse would, therefore, be from the start of inhalation up to the point during inspiration when the volume remaining to be inspired equals the end volume. Atomisation would then be stopped and the remaining end volume would clear the atomised medication from the device and the upper airways of the patient and into the lungs. Thus, the percentage of inspiration in which atomised medication is delivered is maximised, thereby minimising treatment time and still avoiding wastage of medication. The length of the atomisation pulse is dependent upon the patient's inspiratory tidal volume. The nebuliser must therefore measure the patient's tidal volume, preferably on a breath by breath basis so as to calculate, for example from the previous three breaths, an average inhalation volume for the next breath. Thus, the atomisation pulse time will be calculated as follows:

$$\text{Pulse time} = \text{mean inspiratory time} \times \frac{(\text{mean tidal volume} - \text{end volume})}{\text{mean tidal volume}}$$

A timer is included in the nebuliser connected to the pressure sensor 109 (shown in FIG. 7) in order to measure the duration of inspiration. Storage means are also included in the nebuliser in which an estimate of the end volume of a particular patient is stored. Since this figure is a constant value for a particular patient, this can be entered at the beginning of a course of treatment, and is estimated on the basis of the size of the patient. The nebuliser includes a means for measuring the tidal volume of a patient. According to one form of the invention, the patient's inspiratory flow is monitored continuously, typically every ten milliseconds, and this is integrated over the inspiratory duration. Another, simpler, way of measuring the tidal volume of a patient is described later in this specification.

The nebuliser also includes means for calculating the atomisation pulse time on the basis of the duration of inspiration, the tidal volume and the end volume. The calculation means carries out the calculation outlined above.

In view of the fact that the nebuliser adapts to the breathing pattern of a patient, when the patient starts breathing, no atomisation takes place during the first three breaths. Those first three breaths are used to analyse the breathing pattern of the patient. The flow rate of the first three breaths are measured, and from this, the duration of the inhalation phase of the first three breaths are calculated, and an average found. The average duration of inhalation is then used in the calculation to determine the pulse length of atomisation during the fourth breath. In addition, as the patient continues to breathe in and out, the previous three breathing patterns are measured and used to calculate the next pulse duration. Thus, if a patient's breathing pattern improves during treatment, the nebuliser will adapt to this change in order to optimise the dose administered during each breath.

Figure 8:
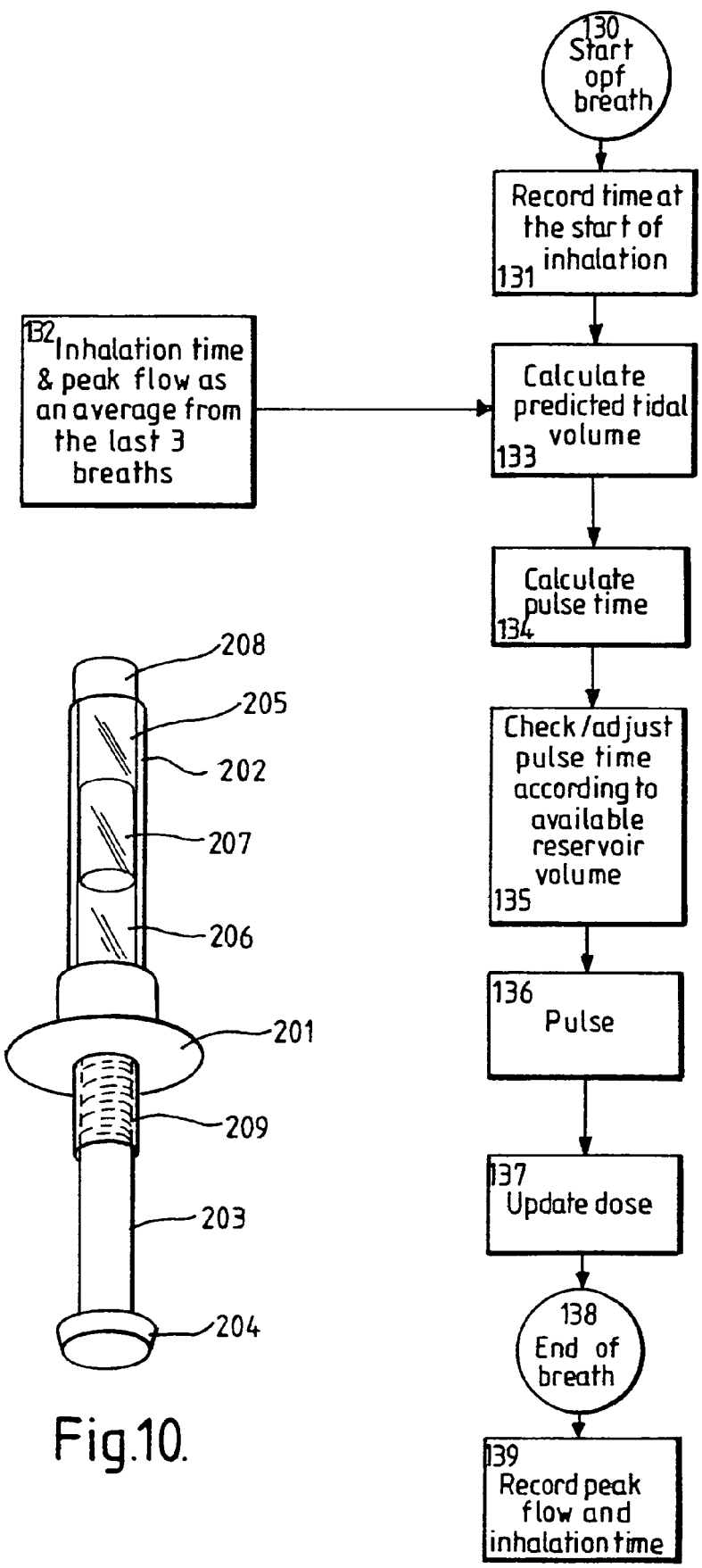
FIG. 8 is a flow diagram of the operation of an atomiser of the type shown in FIGS. 6 and 7.
Figure 9:
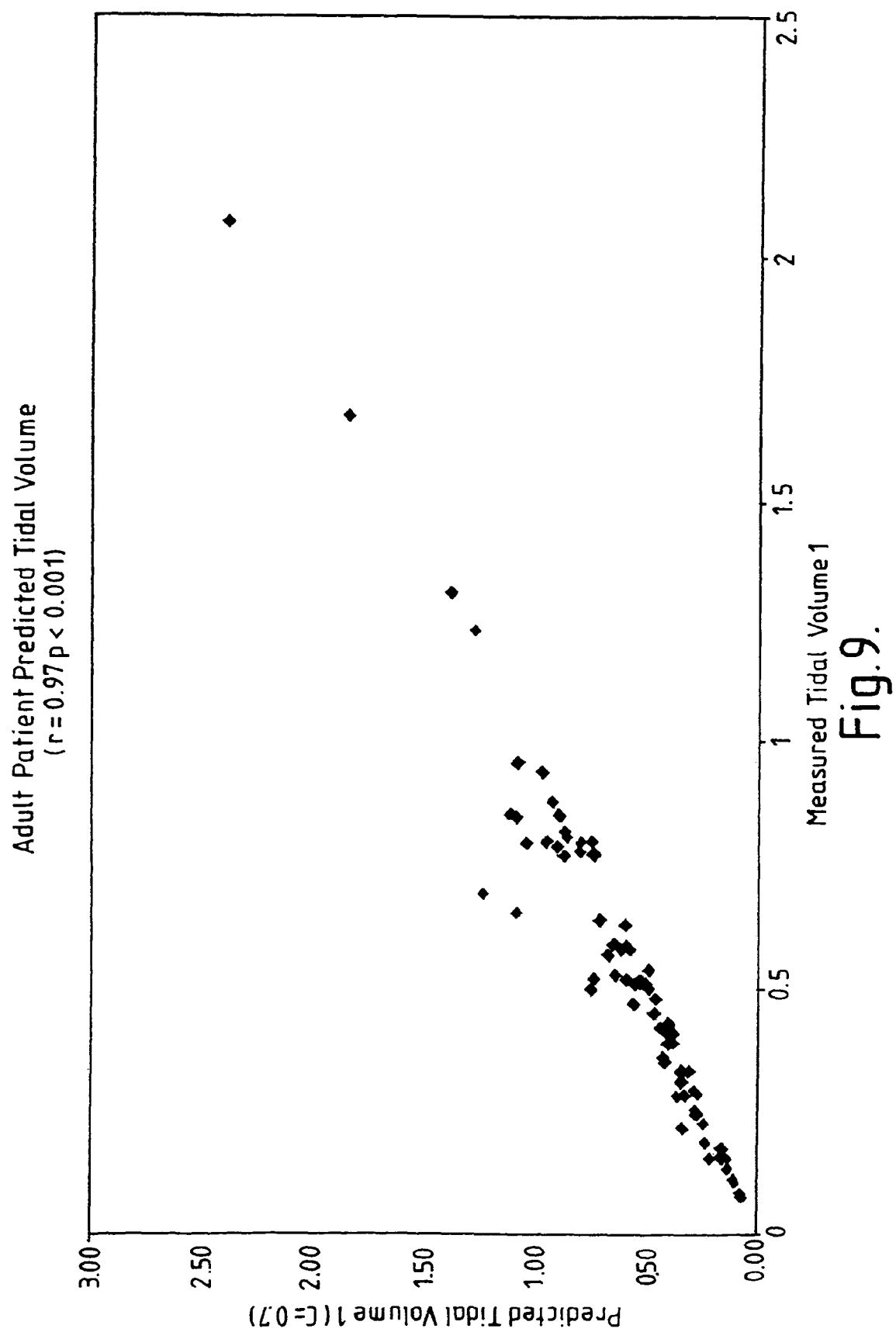
FIG. 9 is a graph showing the predicted tidal volume cluttered against the measured tidal volume.

Referring now to FIG. 8, the steps taken by the nebuliser, and by the patient are described. The first operation, box 130 represents the patient starting to inhale. The timer records the time at which inhalation starts as shown in box 131, and during inhalation, a calculation is performed to predict the tidal volume of the patient as shown in box 133. This step will be described in more detail later in a specification, but it will be noted that the calculation requires data to be included in the calculation including the inhalation time and peak flow as an average from the last three breaths, as shown in box 132. The pulse time is then calculated as shown in box 134, and the pulse time is adjusted, as shown in box 135 in the event that the pulse length would exhaust an accumulator from which is pressurised air is supplied to the nebuliser. The pulse of atomisation occurs during inhalation, and after it has stopped, a calculation is carried out to determine what dose has been atomised. At the end of the breath as shown in box 138, details of the peak flow of the patient inhalation, and the duration of inhalation are recorded so that calculations determining pulse length may be made for subsequent breaths. This is shown in box 139.

Reference is made above to the simpler prediction of tidal volume. As will be appreciated, measuring tidal volume by integrating measured flow rate over the time of inspiration requires considerable processing power and is relatively expensive. A simpler method of determining the tidal volume is proposed which requires much simpler calculations and much simpler measurements to be made for use in such a calculation. To carry out the measurement, the nebuliser includes a peak flow detector for detecting the peak flow rate of inspiration.

The calculated, or predicted tidal volume is derived from the peak flow measured by the peak flow detector, and the duration of inspiration measured by the timer. The tidal volume calculation means carries out the following calculation:

$$\text{Predicted tidal volume} = C \times \text{Mean Peak Flow} \times \frac{\text{Inspiratory Time}}{60}$$

C is a constant and it is found that C=0.7

FIG. 9 is a graph of the predicted tidal volume against measured tidal volume. Each point on the graph represents a patient whose tidal volume has been measured by a complex tidal volume calculation by integration of the patient's inspiratory flow over the duration of inhalation, and the predicted tidal volume according to the new, simpler method of calculation. It will be seen that the predicted tidal volumes are extremely accurate, and so the predicted tidal volume may be included in the calculation of atomisation pulse time.

The use of this invention provides a particularly effective therapy when multiple inhalations are required, as is usually the case for systemic drug delivery via the lung alveoli or local drug delivery to the lung for respiratory disease, as in the case of the use of anti-infective drugs. It significantly reduces the volume of drug required because there is reduced wastage as no aerosol is generated on exhalation and lost to the environment, but only on the initial phase of inhalation. Also, such an atomiser informs the patient when treatment is complete and the correct dose is received. This prevents the patient from receiving too much of the medication or an overdose, and ensures that enough of the drug is received for proper therapeutic effect. With antibiotic drugs, for example, where such large quantities are required to be administered, it has been unexpectedly found in tests that there is a significant increase in a patient's compliance with the treatment regimen, at least to 80% of treatments and normally to at least 90% of treatments.

FIG. 10 shows a drug package suitable for storage of most aerosol drug products, including anti-infectives and proteinaceous material, and their administration into the drug delivery apparatus. Many aerosol drug products, when in solution, have a limited stability and shelf-life. Consequently, such products, as stated herein, are supplied in a dried form, such as a powder, crystalline, micronized or lyophilized solid material, which must be reconstituted prior to inhalation. Other aerosol drug products in their final liquid formulation may have a limited shelf-life as well. Consequently, such products require their ingredients to be admixed at the time of inhalation. FIG. 10 shows an example of a drug package suitable for supplying aerosol drug products that require packaging in a dried form or require their liquid ingredients to be separated until use. Those skilled in the art will appreciate that FIG. 10 shows a drug package that can integrate with a drug delivery device to enable the proper and accurate administration of a reconstituted dried aerosol solution or even an aerosol drug packaged therein as two separate liquid components. The package includes a body 201 from which extends a tube 202. From the opposite side of the body 201 extends a piston 203, which may be pushed through the body 201 and into the tube 202. For this reason, the piston 203 includes a knob 204 so that the fingers of a person can push the piston 203 inwardly by squeezing the knob and a flange of the body 201 together.

The tube 202 is divided into a first chamber 205 and a second chamber 206 separated by a stopper 207. The end of the tube 202 furthest from the body 201 is closed by a closure 208. The end of the tube 202 is designed to integrate with the drug delivery apparatus at either the mouthpiece, baffle, medication chamber, or other suitable location so as to provide a direct connection for the liquid or reconstituted aerosol drug product to enter the drug delivery apparatus. The first chamber 205 contains the solid drug product and the second chamber 206 contains a diluent/solvent in which the dry/dried product is soluble. Alternatively, the first chamber 205 contains a liquid constituent of drug product and the second chamber 206 contains the other miscible liquid constituent. The stopper (207) keeps the two apart until mixing is required.

The piston 203 is threaded towards the end closest to the body 201 and the body 201 includes internal threads which engage with the threads 209 of the piston 203.

In use the piston 203 is turned with respect to the body 201 so that the piston pushes the material from the second chamber 206 past the stopper 207 into the first chamber 205 where mixing of either the solid and liquid or liquid and liquid components of the aerosol drug product takes place. The piston is then pushed through the body 201 such that the liquid drug product is expelled from the tube 202 at the end which contains the closure and attachment (integration) with the drug delivery apparatus or atomizer. The liquid aerosol product is thus expelled directly and accurately into the atomizer.

It can also be appreciated by one skilled in the art that the drug package suitable for storage of most aerosol drug products and their expellsion into the atomizer, may be designed with only a single chamber, where the first chamber 205 and second chamber 206 are not separated by a stopper 207. This one part drug package would be suitable for use with liquid aerosol drug products that can be packaged in their final formulation, i.e., the formulation that is inhaled and dispensed directly and accurately into the atomizer.

In order to describe the advantageous effect of the apparatus, examples of the drugs which may be used will now be described. The drugs concerned require treatment over multiple breaths due to the volume of drug delivered. Solution based formulations require between 0.1 and 0.5 ml to be delivered, and powder-based drugs between 1 and 5 mgs. Most of such drugs are used for prophylactic treatment and do not give any direct feedback in terms of benefit at the time of treatment nor negative feedback such as coughing.

In the following, it should be understood that the "lung dose" is the amount of a drug which reaches the lungs, and that to achieve the lung dose, it is necessary to deliver more than that since some of the drug will not reach the lungs.

An important drug which is delivered to the lungs is Tobramycin. A typical treatment of Tobramycin requires the delivery of 30 mgs to the lungs. A typical nebuliser delivers about 10% to the lungs which means that 300 mgs of Tobramycin must be nebulised. 300 mgs would normally be dissolved in 5 mls of 0.225% NaCl having a pH of 5.5 to 6.5. Thus, the concentration is 60 mg/ml. However, the use of the present invention allows considerably less of the drug to be used. Since delivery efficiency is at least 80%, if a dose of 15 mgs is required to reach the lungs, only 19 mgs needs to be delivered. The formulation can be the same as is described above in connection with existing nebulisers, but the amount of the drug used is much less. Of course, in addition to the amount of the drug which is dispensed, a delivery apparatus will have a dead volume which is residual and remains in the delivery device even if delivery continues. For example, with some pneumatic or jet-type nebulisers, the dead volume may be as much as 0.8 ml. However, a mesh-type atomiser could have a dead volume of at little as 0.1 ml. Thus, the amount of the drug which is actually placed in the drug delivery device may be 1.01 mls for the jet-type nebuliser (0.8 ml dead volume+0.21 ml for delivery), or 0.42 ml for the mesh-type atomiser (0.1 ml dead volume+0.32 ml for delivery). Of course, other types of drug delivery device will have different dead volumes, and so the actual amount of the drug supplied for those devices will be different.

To provide effective control of one of the main infective lung organisms "*Pseudomonas aeriginosa*" in cystic fibrosis patients the concentration of Tobramycin in the lung fluid must exceed the minimal inhibitory concentration (MIC) for the organism to be eliminated. For Tobramycin the MIC level is typically required to be >16 μg/ml for 90% of organisms, and the MIC concentration should be maintained at this level for 120 minutes.

To compare the performance of a conventional nebulizer and a high compliance system according to this invention using Tobramycin 8 patients received either 300 mg/5 ml via conventional nebulizer or 30 mg delivered dose via the high compliance system. The mean sputum tobramycin concentrations at 2 hours were 128 μg/g for the conventional nebulizer and 98 μg/g for the high compliance system. This study may indicate that an even lower dose may be acceptable to achieve the MIC level when delivered with a high compliance system such as disclosed in this invention, in the range 5-30 mg Tobramycin.

Tobramycin is a stable drug and can be packaged as a unit dose solution in a one-part package as described above in connection with a modified FIG. 10 or in a single glass or plastic unit dose vial.

If the drug Colistin is used (colistin sulphomethate) then the maximum daily dose is 6 million units in three treatments. This is an equivalent lung dose of 600,000 U per day, but with the present invention delivering 300,000 U per day at an efficiency of over 80% allows only 375,000 U to be delivered by the atomiser per day over two treatments of 187,000 U per treatment. Thus, a very significant reduction in the amount of the drug is achieved. Four examples of the drug formulation for Colistin are described below. In the first formulation, one million units of Colistin is dissolved in two mls of 0.9% NaCl. In the second, the Colistin is dissolved in a two mls solution made up from 0.75 ml of 0.9% NaCl and 1.275 ml of water.

Alternatively, the formulation can include an additional bronchial dilator such that the Colistin is dissolved with 2.5 mgs of salbutamol in 2.5 mls of 0.9% NaCl, or alternatively with 2.5 mgs of salbutamol dissolved in 0.75 mls of 0.9% NaCl plus 1.275 mls of water. Finally, the Colistin can be dissolved in a solution including 2.5 mg of DNase in 2.5 mls of 0.9% NaCl. Since Colistin is not stable in solution, it is supplied as a powder which must be pre-mixed with a dilutant either supplied in a different vial, or in a two-part package, as described above in connection with FIG. 10. In the present application, the actual volume of the Colistin formulation required to be placed in the drug delivery apparatus may be 0.48 ml for a mesh atomiser, or 1.18 mls for a jet nebuliser, much less than in conventional nebulisers. Of course, other drug delivery apparatus will require different volumes according to their dead volume.

Another drug which can be delivered in the same way with similar advantages is DNase. The required lung dose in a normal nebuliser is 0.25 mgs. 2.5 mgs of DNase in 2.5 mls 0.9% NaCl is required in normal (conventional) nebulisers. However, in the present invention a lung dose of 0.125 mg delivered with 80% efficiency requires a dose of only 0.156 mg, much less than in conventional nebulisers. The high efficiency is the result of a particle size of the drug being within a narrow range of sizes, about 3 microns in diameter. That way, 80% of the delivered drug reaches the lungs and stays there. Only 20% loss occurs due to impaction and exhalation.

Depending on the dead volume, the amount of drug supplied for a jet nebuliser may be 1.06 mls, and for a mesh atomiser 0.26 ml. Other drug delivery apparatus will require different volumes depending on their dead volume.

Approximately 38% of patients show a greater than 10% change in $FEV_1$ over baseline when starting rhDNase therapy. Some patients may not respond to inhaled therapies due to poor nebulizer techniques such as nose breathing, talking, coughing, resulting in poor inhalation compliance.

A study to assesses the response to rhDNase delivered by a system according to this invention in patients who have previously failed to respond to therapy with conventional nebulizer devices.

Eight Adult CF patients who had previously failed to respond to rhDNase therapy (mean response to therapy 4.17% change in $FEV_1$) used aerosolized rhDNase delivered for 10 days using 0.25 ml/0.25 mg of the formulation. the device. Mean change in $FEV_1$ was 11.51%.

This result shows that in CF patients who have previously failed to respond to inhaled therapies, have an improved response with a high compliance delivery system, compared to their conventional nebulizer. This study may indicate that an even lower dose may be acceptable when delivered with a high compliance system such as disclosed in this invention, in the range 0.06/0.25 mg rhDNase.

A further suitable drug is A1AT (Alpha 1 Antitrypsin) for which the lung dose for a conventional nebuliser is typically 20 mgs requiring nebulisation of some 200 mg of the drug in 4 ml of 0.9% NaCl. Because of the delivery efficiency of the delivery device according to the present invention, a lung dose of 10 mgs is required with the nebuliser delivering 12.5 mgs of the formulation having a concentration of 50 mg per ml of 0.9% NaCl. In our jet-type nebuliser, the volume of drug required will be 1.05, but in a mesh type atomiser will be 0.35 ml. Other drug delivery apparatus will require different volumes according to their dead volumes.

A1AT is supplied as a powder requiring dilution with water. A two-part package such as is disclosed in FIG. 10 will be suitable for a supply of the drug dilutant.

Another drug is cyclosporine which is normally delivered by a nebuliser requiring a lung dose of 100 mgs at a concentration of 125 mgs per ml. Normally, 500 mg of cyclosporine in 4 ml of propylene glycol must be nebulised. A lung dose from the present invention is 50 mgs using only 62 mgs of the same formulation.

The amounts supplied for a typical jet nebuliser will be 1.3 mls, and for a mesh type atomiser 0.6 ml. Other drug delivery apparatus will require a different volume depending on its dead volume.

Budesonide is a corticosteroide with a high topical anti-inflammatory activity, it is important in the management of asthma. To be effective steroids must be delivered over long periods ranging from months to years. However it is important to minimise the dose delivered as there can be significant side effects on the adrenal function, calcium metabolism and growth rate in children. There are also local side effects including irritation in the throat, candidiosis, and dysphonia.

Budesionide for nebulisation is typically formulated as 1000 mg, 500 mg or 250 mg in 2 ml for conventional nebulizers.

A study in 125 children with asthma using the system disclosed in this patent delivered three different regimes of a short duration (2-12 weeks) high delivered daily dose 200 μg followed by a long duration (12-22 weeks) low daily dose delivered dose 50 μg. Their treatment compliance was monitored electronically and their asthma symptoms by the parents using a visual analogue score. The treatment compliance over the study was 80/90% and the asthma scores reduced from a baseline of 1.23/1.27 to 0.23/0.43.

The study in 481 children with asthma using conventional nebulizers delivered five different regimes. Nominal nebulizer doses were in the range 250/1000 μg daily and placebo over a 12 week period. Their asthma symptoms by the parents using a visual analogue scores, the asthma scores reduced from 1.21/1.33 to 0.87/0.93.

The comparative data in table 1 shows that the system according to this invention improved asthma scores by approximately twice as much as the conventional nebulizer using a low long-term daily dose. This study may indicate that an even lower daily dose may be acceptable when delivered with a high compliance system such as disclosed in this invention, in the range 12-50 μg budesonide. When delivered from a formulation of 500 μg/ml would required only 0.024/0.1 ml of formulation.

This invention can also be applied to other corticosteroides such as Fluticasone currently delivered by conventional nebulizer in a formulation of 250 μg/2000 μg in 2.5 ml. A delivered daily dose in the range 6-50 μg may be required, from an 800 μg/ml formulation would require 0.0075/0.063 ml.

TABLE 1

Budesonide Nebulising Suspension
Study results daytime asthma symptom scores
(Visual analogue range 0-3 where 0 is no symptoms)

| | Conventional Nebuliser Placebo | 250 μg Once daily | 250 μg Twice daily | 500 μg Twice daily | 1000 μg Once daily | Improved Invention System 200/50 μg 2/22 weeks | 200/50 μg 6/18 weeks | 200/50 μg 12/12 weeks |
|---|---|---|---|---|---|---|---|---|
| Baseline at entry | 1.27 | 1.21 | 1.31 | 1.33 | 1.28 | 1.23 | 1.26 | 1.27 |
| End of Study | 1.08 | 0.93 | 0.91 | 0.87 | 0.91 | 0.23 | 0.43 | 0.36 |
| Change | 0.19 | −0.28 | −0.4 | −0.46 | −0.37 | −1 | −0.83 | −0.91 |

Other drugs suitable for use are antiviral/antiinfective drugs Gamma Interferon (IFN*), Synagis™ Virazole® and SuperVent™, antifungal drugs such as AmBiosome®, corticosteroids such as Budesonide®, Surfactant drugs Exosurf® and Surfaxin™. Other drugs suitable for use are hormones, including growth hormone, Erythropoitin, Parathyroid Hormone, Lureinizing Hormone Releasing Hormone (LHRH). Also drugs for pulmonary hypertension (PPH) including Iloprost, Flolan and UT15, and for pain control opiates and cannabinoids including Dronabinol (THC), Morphine and Marinol®.

Other drugs suitable are insulin for diabetics and Calcitonin for osteoporosis.

The invention claimed is:

1. A drug delivery apparatus comprising:

a drug delivery device for selectively delivering drug-laden air or air not laden with the drug;

a sensor for monitoring a breathing pattern of a patient;

a controller arranged to control the drug delivery device based on a length of at least one previous inhalation of the patient to deliver drug-laden air in pulses which begin when the patient is monitored by the sensor to begin inhalation, the pulses having a duration which is adjusted by the controller on the basis of the monitored breathing pattern of the patient and the length of the at least one previous inhalation, wherein the pulse duration is determined based upon a tidal volume and an end volume of the patient, and wherein if a monitored inhalation is not suitable for drug delivery the controller controls the drug delivery device to abort a pulse corresponding to the monitored inhalation;

a feedback indicator which indicates to the patient whether a pulse of drug-laden air is currently being delivered;

a dose calculator which calculates a dose delivered to the patient;

an indicator which indicates to the patient when a desired dose has been delivered; and a drug formulation in which NaCl and tobramycin are dissolved in a solvent, wherein a delivery efficiency of the drug formulation is at least 80 percent.

2. The drug delivery apparatus according to claim 1, wherein the drug formulation includes about 19 mg tobramycin and the solvent is about 0.3 ml in volume.

3. The drug delivery apparatus according to claim 1, wherein the drug formulation further comprises an additional amount of between about 6 and 50 mg tobramycin in about 0.1 to 0.8 ml solution which fills a dead volume of the delivery apparatus and which is residual once all of the drug which can be delivered has been delivered.

4. The drug delivery apparatus according to claim 1, wherein the concentration of tobramycin is about 60 mg/ml.

5. A drug delivery apparatus comprising:
a drug delivery device for selectively delivering drug-laden air or air not laden with the drug;
a sensor for monitoring a breathing pattern of a patient;
a controller arranged to control the drug delivery device based on a length of at least one previous inhalation of the patient to deliver drug-laden air in pulses which begin when the patient is monitored by the sensor to begin inhalation, the pulses having a duration which is adjusted by the controller on the basis of the monitored breathing pattern of the patient and the length of the at least one previous inhalation, wherein the pulse duration is determined based upon a tidal volume and an end volume of the patient;
a feedback indicator which indicates to the patient whether the monitored breathing pattern is effective for inhaling drug-laden air or not;
a dose calculator which calculates a dose delivered to the patient;
an indicator which indicates to the patient when a desired dose has been delivered; and
a drug formulation including Alpha 1 Antitrypsin in an aqueous solution, wherein a delivery efficiency of the drug formulation is at least 80 percent.

6. The drug delivery apparatus according to claim 5, wherein the drug formulation includes about 12.5 mg Alpha 1 Antitrypsin and the aqueous solution has a volume of about 0.25 ml.

7. The drug delivery apparatus according to claim 6, wherein the drug formulation further includes an additional amount of between 0.1 ml and 0.8 ml of solvent.

8. A drug delivery apparatus comprising:
a drug delivery device for selectively delivering drug-laden air or air not laden with the drug;
a sensor for monitoring a breathing pattern of a patient;
a controller arranged to control the drug delivery device based on a length of at least one previous inhalation of the patient to deliver drug-laden air in pulses which begin when the patient is monitored by the sensor to begin inhalation, the pulses having a duration which is adjusted by the controller on the basis of the monitored breathing pattern of the patient and the length of the at least one previous inhalation, wherein the pulse duration is determined based upon a tidal volume and an end volume of the patient, and wherein if a monitored inhalation is not suitable for drug delivery the controller will control the drug delivery device to abort a pulse corresponding to the monitored inhalation;
a feedback indicator which indicates to the patient whether a pulse of drug-laden air is currently being delivered;
a dose calculator which calculates a dose delivered to the patient;
an indicator which indicates to the patient when a desired dose has been delivered; and
a drug formulation including Budesonide in a solvent, wherein a delivery efficiency of the drug formulation is at least 80 percent.

9. The drug delivery apparatus according to claim 8, wherein the drug formulation includes about 25 μg of Budesonide and a volume of the solvent is about 0.05 ml.

10. A drug delivery apparatus comprising:
a drug delivery device for selectively delivering drug-laden air or air not laden with the drug;
a sensor for monitoring a breathing pattern of a patient;
a controller arranged to control the drug delivery device based on a length of at least one previous inhalation of the patient to deliver drug-laden air in pulses which begin when the patient is monitored by the sensor to begin inhalation, the pulses having a duration which is adjusted by the controller on the basis of the monitored breathing pattern of the patient and the length of the at least one previous inhalation, wherein the pulse duration is determined based upon a tidal volume and an end volume of the patient, and wherein if a monitored inhalation is not suitable for drug delivery the controller will control the drug delivery device to abort a pulse corresponding to the monitored inhalation;
a feedback indicator which indicates to the patient whether a pulse of drug-laden air is currently being delivered;
a dose calculator which calculates a dose delivered to the patient;
an indicator which indicates to the patient when a desired dose has been delivered; and
a drug formulation including fluticasone in solution, wherein a delivery efficiency of the drug formulation is at least 80 percent.

11. The drug delivery device as recited in claim 1, wherein the pulse duration is calculated as:

$$\text{Pulse duration} = \text{mean inspiratory time} \times (\text{mean tidal volume} - \text{end volume})/\text{mean tidal volume}.$$

12. The drug delivery device as recited in claim 5, wherein the pulse duration is calculated as:

$$\text{Pulse duration} = \text{mean inspiratory time} \times (\text{mean tidal volume} - \text{end volume})/\text{mean tidal volume}.$$

13. The drug delivery device as recited in claim 8, wherein the pulse duration is calculated as:

$$\text{Pulse duration} = \text{mean inspiratory time} \times (\text{mean tidal volume} - \text{end volume})/\text{mean tidal volume}.$$

14. The drug delivery device as recited in claim 10, wherein the pulse duration is calculated as:

$$\text{Pulse duration} = \text{mean inspiratory time} \times (\text{mean tidal volume} - \text{end volume})/\text{mean tidal volume}.$$

* * * * *